United States Patent [19]
Andre et al.

[11] Patent Number: 5,583,634
[45] Date of Patent: Dec. 10, 1996

[54] PROCESS FOR ELEMENTARY ANALYSIS BY OPTICAL EMISSION SPECTROMETRY ON PLASMA PRODUCED BY A LASER IN THE PRESENCE OF ARGON

[75] Inventors: Nadine Andre, Villeneuve-La-Garonne; Patrick Mauchien, Palaiseau; Alexandre Semerok, Gif-Sur-Yvette, all of France

[73] Assignee: Commissariat a l'Energie Atomique, Paris, France

[21] Appl. No.: 339,232

[22] Filed: Nov. 10, 1994

[30] Foreign Application Priority Data

Nov. 19, 1993 [FR] France ..................... 93 13855

[51] Int. Cl.⁶ ........................................... G01N 21/63
[52] U.S. Cl. ............................................ 356/318
[58] Field of Search ..................... 356/317, 318

[56] References Cited

U.S. PATENT DOCUMENTS 4,645,342  2/1987  Tanimoto et al. ............... 356/318

FOREIGN PATENT DOCUMENTS 2-254345  10/1990  Japan ............................. 356/318

OTHER PUBLICATIONS

Applied Spectroscopy, vol. 42, No. 7, 1988, Peter Arrowsmith, et al, "Entrainment and Transport of Laser Ablated Plumes for Subsequent Elemental Analysis", pp. 1231–1239.

Applied Spectroscopy, vol. 47, No. 5, May 1993, C. Aragon, et al., "Determination of Carbon Content in Molten Steel Using Laser–Induced Breakdown Spectroscopy", pp. 606–608.

Applied Spectroscopy, vol. 46, No. 9, Sep. 1992, J. A. Aguilera, et al., "Determination of Carbon Content in Steel using Laser–Induced Breakdown Spectroscopy", pp. 1382–1387.

*Primary Examiner*—F. L. Evans
*Attorney, Agent, or Firm*—Oblon, Spivak, McClelland, Maier & Neustadt, P.C.

[57] ABSTRACT

A process for simultaneously blowing a gas jet onto a sample 6 to be analyzed and subsequently focusing a laser beam 4 onto the sample so as to produce a plasma 12 on the surface of the sample. An analysis is made of the spectrum S' of the light radiation emitted by the plasma and this spectrum analysis provides the basis for determining the composition of the isotopic composition of the sample.

3 Claims, 4 Drawing Sheets

PROCESS FOR ELEMENTARY ANALYSIS BY OPTICAL EMISSION SPECTROMETRY ON PLASMA PRODUCED BY A LASER IN THE PRESENCE OF ARGON

BACKGROUND OF THE INVENTION

1. Field of the Invention

The present invention relates to a process for elementary analysis by optical emission spectrometry on plasma produced by a laser in the presence of argon. It applies to the in situ checking and inspection of samples and the characterization of machined parts. It is more particularly usable in the nuclear industry for the inspection of radioactive materials.

2. Discussion of the Background

It is known to measure the elementary concentrations of elements by a spectrochemical analysis using the emission radiation of a plasma produced by laser. This analytical method is based on a laser ablation, i.e. a tearing away of material under the effect of high heat levels.

The process for analysis by optical emission spectrometry on plasma produced by a laser uses such a laser ablation. It consists of focussing on the surface of the solid to be studied a pulsed laser beam having a high peak power (typically a few GW/cm$^2$) so as to produce a plasma constituted by chemical elements present in the first microns of the surface. This plasma emits a light radiation, the analysis of the atomic lines thereof making it possible to obtain information on the concentration of the different elements in the solid.

However, such a process does not have a very high sensitivity which, for certain analytical cases, is completely inadequate. In addition, it is known that certain gases constitute a more favourable atmosphere for spectral analyses than the natural atmosphere (i.e. air).

A procedure for improving the intensity of the lines during spectral analyses and therefore for improving the accuracy of the measurements, consists of placing the sample to be analysed in a closed container filled with a gas and more particularly argon.

According to this procedure the measurements are performed in a confined atmosphere, so that it can only be carried out in the laboratory.

DESCRIPTION OF THE INVENTION

The present invention aims at obviating these disadvantages by proposing a process for the measurement of the concentration of elements using an argon jet and which can be performed in situ.

More specifically, the invention relates to a process for the elementary analysis of a sample. This process, performed in a natural atmosphere, consists of simultaneously blowing a gas jet onto the sample to be analysed and focussing a laser beam onto said sample to be analysed so as to produce a plasma on the surface of said sample, analysing a spectrum of the light radiation emitted by the plasma and determining, on the basis of said spectrum analysis, the elementary composition of the sample.

Advantageously, the gas jet blown onto the sample is an argon jet.

Therefore this process has the advantage of being performed in a natural atmosphere (or unconfined atmosphere). It also has the advantage of requiring no contact with the sample and of not requiring any prior chemical preparation of the samples. Moreover, its performance and operation are simple, its sensitivity is good and the measurements are rapidly obtained. Therefore this process can easily be carried out in situ.

Additionally, said process has the advantage of being applicable to numerous types of conductive or non-conductive materials, as well as to materials considered to be difficult to analyse such as ceramics, glasses, composites or radioactive materials, because the measurements are performed without any contact taking place.

DETAILED DESCRIPTION OF THE PREFERRED EMBODIMENTS

Figure 1:
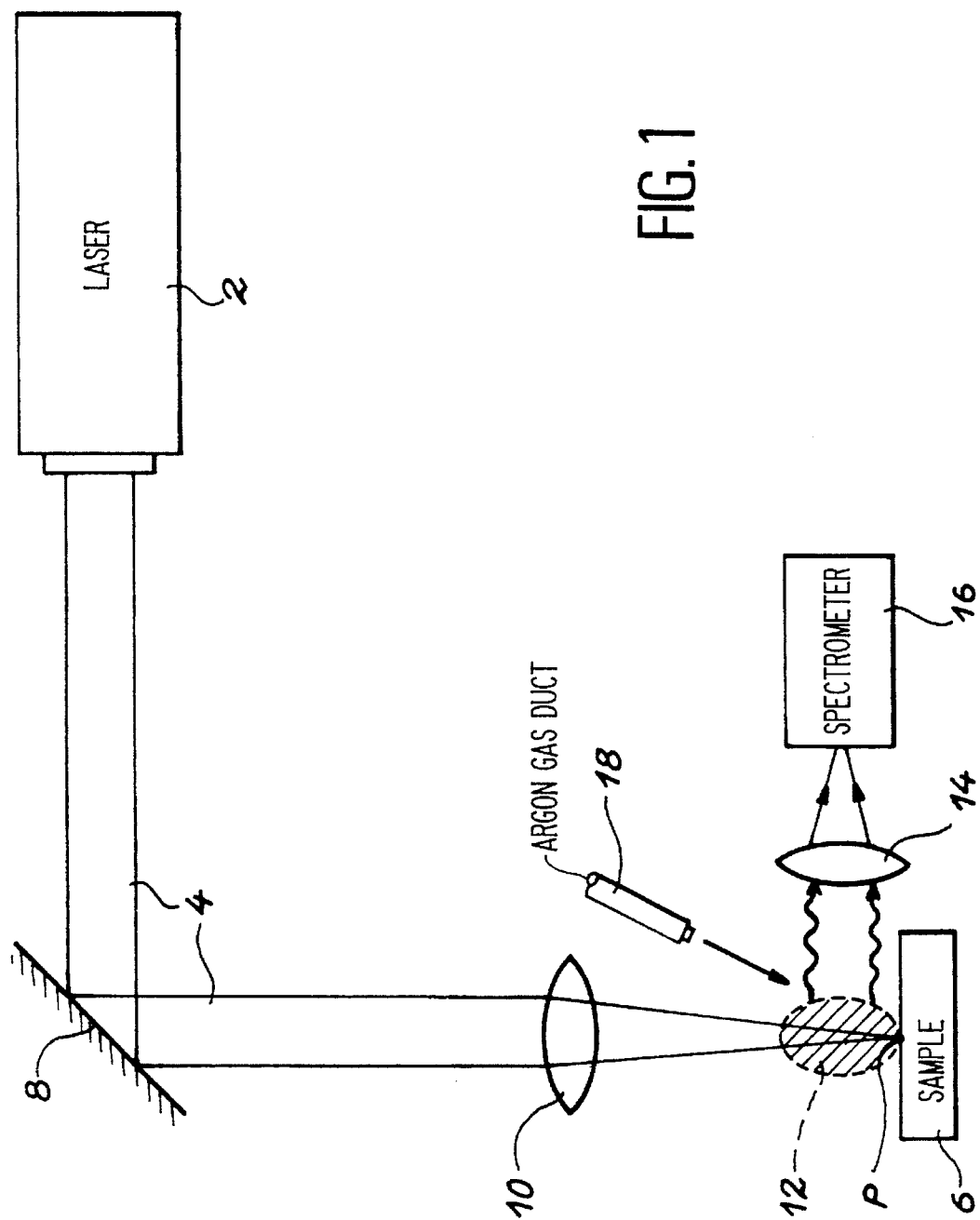
FIG. 1 is a diagram of the equipment performing the process of the invention.

FIG. 1 is the basic diagram of equipment performing the process according to the invention. A laser source 2 emits a pulsed laser beam 4 directed towards the sample 6. This laser beam 4 has a high peak power of a few GW/cm$^2$. According to an embodiment, the laser beam 4 is directed directly at the sample 6. According to another embodiment shown in FIG. 1, the laser beam 4 is directed at a mirror 8 which, by reflection, orients the beam 4 towards the sample 6.

This beam 4 is focussed towards the sample 6 by means of a focussing objective or lens 10, which can e.g. be a simple convergent lens or a reflecting microscope objective of the cassegrain type or numerous other types of focussing objectives.

The energy deposited on the sample 6 by the laser beam 4 is a few Joules/cm$^2$ and brings about the tearing away of material and the formation of a light plasma 12. At least part of the light emitted by the plasma 12 is focussed by the optical system 14 and then collected by the spectrometer 16.

This spectrometer 16 ensures the separation of the different radiations from the plasma 12. Processing means, not shown in FIG. 1, ensure the spectral analysis of the emission lines obtained at the output of the spectrometer 16. It is thus possible to determine the concentration of the different elements forming the sample.

Argon jet projection means are shown in FIG. 1 and can e.g. be constituted by a gas duct 18 such as is conventionally used in equipment requiring a gas supply. However, said duct 18 must have an adequate rigidity to blow the argon jet 20 at the impact point P of the laser beam 4 onto the sample 6. A weak argon jet 20 blown at point P is sufficient for creating conditions which are more favourable for the spectral analysis of the light emitted by the plasma 12.

Such an argon jet 20 also has the advantage of protecting the focussing objective to from particles of material torn away by the laser beam and projected towards said objective 10, said projected particles being deflected from their path by the argon jet.

In order to obtain optimum results, it is possible to perform this elementary analysis process by e.g. using an ultraviolet laser beam supplying a 266 nm line and a cassegrain reflecting microscope objective making it possible to obtain, on the sample, a focal spot with a diameter of 10 μm. This makes it possible to produce a plasma, whose diameter does not exceed 200 μm, the plasma diameter having to be smaller than the diameter of the argon jet blown onto the sample.

The sensitivity of the measurements can be further increased by choosing an optimum argon flow rate, which is approximately 3 l/mn.

Figure 2:
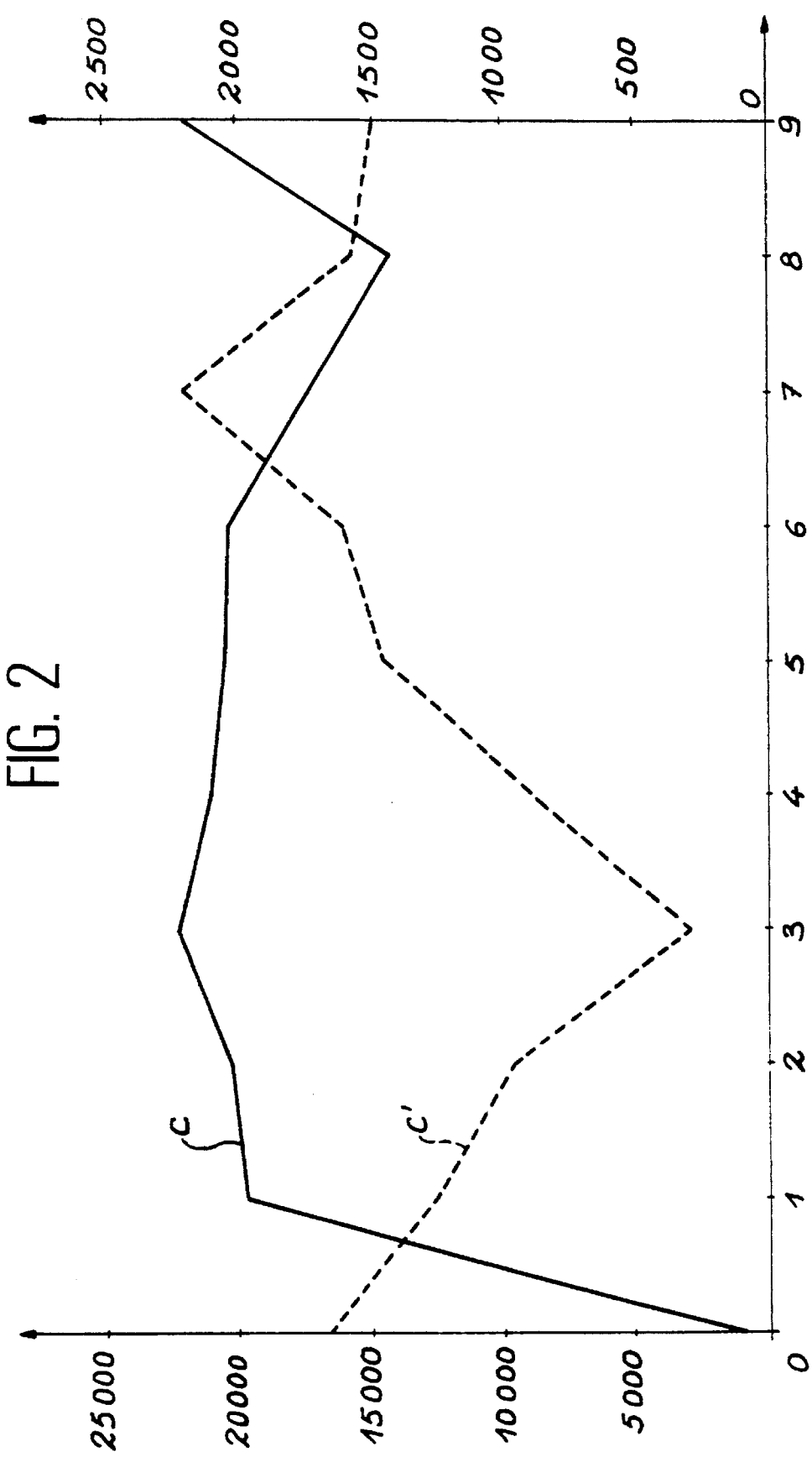
FIG. 2 shows the intensity curves of the emission signal and the standard deviation as a function of the argon flow rate.

FIG. 2 shows a curve representing the intensity of the emission signal as a function of the flow rate of the argon jet blown onto the sample. More specifically, on the abscissa is plotted the argon flow rate in liters per minute and on the ordinate, on the one hand, the emission intensity and, on the other, the standard deviation of the measurements obtained. Thus, curve C represents the intensity of the emission signal which is at a maximum for an argon flow rate of 3 l/mn. The dotted line curve C' represents the standard deviation between the measurements, which is at a minimum for a 3 l/mn argon flow rate.

Figure 3:
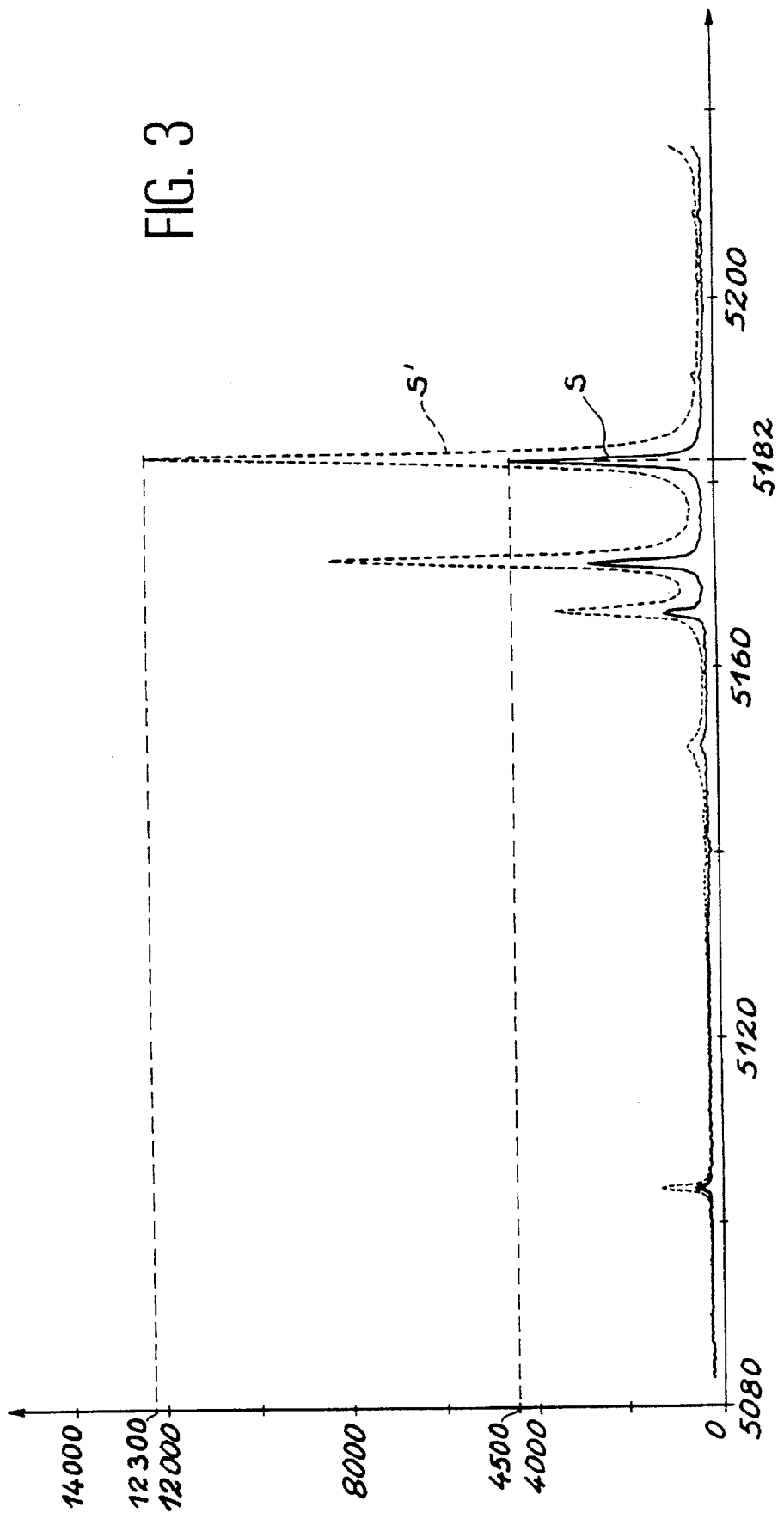
FIG. 3 shows the spectra of the same sample obtained by processes respectively using and not using an argon jet.
Figure 4:
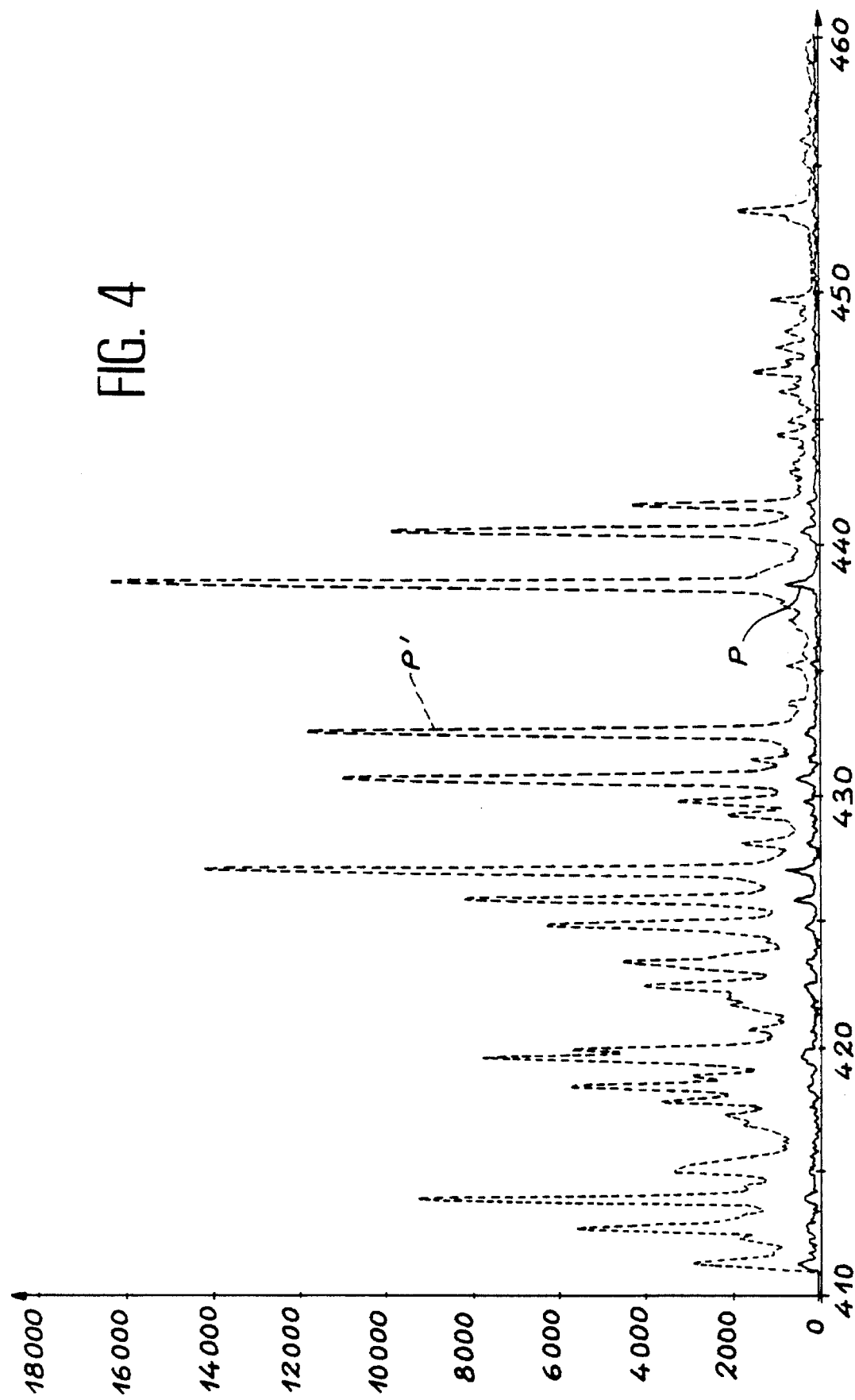
FIG. 4 shows the spectra of an iron sample obtained respectively without an argon jet and with a 3 1/mn argon jet.

To demonstrate the importance of the choice of an optimum flow rate, FIGS. 3 and 4 show emission spectra of the plasma, respectively for a random argon flow rate and for an argon flow rate close to 3 l/mn.

More specifically, FIG. 3 shows the plasma emission spectra of the same sample produced with and without an argon jet. The spectrum S, shown in continuous line form, corresponds to an emission spectrum of the plasma of a sample analysed in a natural atmosphere (air) without an argon jet. The spectrum S' in dotted lines, corresponds to an emission spectrum of the plasma of a sample analysed under the conditions of the invention. Therefore the samples giving spectra S and S' are identical.

With the wavelength of said spectra represented on the abscissa and the emission intensity on the ordinate, it is possible to read from FIG. 3 the intensities of the spectra S' and S given in arbitrary units (a.u.). As the spectra S and S' have emission lines with the same wavelengths, it is clear that the samples from which these spectra are obtained are identical. However, the intensity of the spectrum S' obtained from a sample onto which is blown an argon jet during analysis, is much higher than the intensity of the spectrum S obtained from a sample analysed in a natural atmosphere without an argon jet. More specifically, an emission line at approximately 518.2 nm produced by the sample analysed in a natural atmosphere without the presence of argon (spectrum S) has an intensity of approximately 4,500 a.u. This same emission line at approximately 518.2 nm is emitted with an intensity of approximately 12,300 a.u. when the sample is analysed in the presence of an argon jet. Therefore the intensity ratio of the spectra S and S' is 12,300/4,500, i.e. approximately 2.73.

FIG. 4 shows the emission spectra of plasmas obtained from the same sample and respectively produced without an argon jet and with a 3 l/mn argon jet. The spectrum P, represented in continuous line form, corresponds to the emission spectrum of an iron plasma analysed in a natural atmosphere without an argon jet. The spectrum P', in dotted line form, represents an emission spectrum of an iron plasma analysed under the optimum conditions according to the invention with a 3 l/mn argon jet.

The wavelength of these spectra of iron are represented on the abscissa and the emission intensity on the ordinate, so that for the same emission line, it can be gathered from FIG. 4 that the spectrum P' obtained from an iron sample onto which has been blown an argon jet has a much higher intensity than that of the spectrum P.

More specifically, for an emission line of approximately 438 nm, the spectrum P of iron obtained in a natural atmosphere without argon has an intensity of approximately 800 a.u., whereas the spectrum P' obtained with a 3 l/mn argon jet has an intensity higher than 16,000 a.u.

On simultaneously considering FIGS. 3 and 4, it can effectively be seen that the argon jet is at an optimum for a flow rate of 3 l/mn, because the spectrum P' obtained for a 3 l/mn flow rate argon jet is even more precise than the spectrum S' obtained for an argon jet with a random flow rate.

The process according to the invention consisting of blowing an argon jet onto a sample to be analysed makes it possible to improve the intensity of the emission lines by a factor of approximately 2.5 to 3 for an argon jet with a random flow rate and by a factor of 20 for an optimum flow rate. Therefore the precision of the results is improved.

We claim:

1. Process for the elementary analysis of a sample, characterized in that, in a natural atmosphere, it consists of simultaneously blowing an argon gas jet onto the sample with a flow rate of approximately 3 l/mn to be analyzed and focusing a laser beam onto said sample to be analyzed, so as to produce a plasma on the surface of said sample, analyzing a spectrum, (S') of the light radiation emitted by the plasma and determining, on the basis of said spectrum analysis, the elementary composition of the sample.

2. Process according to claim 1, characterized in that the gas jet blown onto the sample has a diameter larger than that of the plasma obtained on the sample surface.

3. Process according to claim 1, characterized in that the laser beam forms on the sample a focal spot with a diameter of approximately 10 μm.

* * * * *